US010105450B2

(12) United States Patent
Davidson et al.

(10) Patent No.: US 10,105,450 B2
(45) Date of Patent: Oct. 23, 2018

(54) PROMOTER COMPOSITIONS

(71) Applicant: UNIVERSITY OF IOWA RESEARCH FOUNDATION, Iowa City, IA (US)

(72) Inventors: Beverly L. Davidson, Iowa City, IA (US); Edgardo Rodriguez, Iowa City, IA (US); Alejandro Mas Monteys, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/776,421

(22) PCT Filed: Mar. 6, 2014

(86) PCT No.: PCT/US2014/021357
§ 371 (c)(1),
(2) Date: Sep. 14, 2015

(87) PCT Pub. No.: WO2014/149882
PCT Pub. Date: Sep. 25, 2014

(65) Prior Publication Data
US 2016/0022837 A1     Jan. 28, 2016

Related U.S. Application Data (60) Provisional application No. 61/794,818, filed on Mar. 15, 2013.

(51) Int. Cl.
*A61K 48/00* (2006.01)
*C07K 14/47* (2006.01)
*C12N 15/86* (2006.01)

(52) U.S. Cl.
CPC ............ *A61K 48/005* (2013.01); *C07K 14/47* (2013.01); *C12N 15/86* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

| | | | |
|---|---|---|---|
| 5,139,941 A | 8/1992 | Muzyczka et al. | |
| 7,205,146 B1 * | 4/2007 | Keith | C07K 14/47 435/252.1 |
| 2009/0018031 A1 | 1/2009 | Trinklein et al. | |
| 2009/0023674 A1 * | 1/2009 | Pagano | C12N 15/11 514/44 R |
| 2011/0065100 A1 * | 3/2011 | Aldred | C12Q 1/6883 435/6.14 |
| 2012/0100541 A1 | 4/2012 | Ordway et al. | |

FOREIGN PATENT DOCUMENTS

| | | | |
|---|---|---|---|
| EP | 1347046 A1 | 9/2003 | |
| EP | 2221379 A1 | 8/2010 | |
| JP | 2004008216 A | 1/2004 | |
| JP | 2005237384 A | 9/2005 | |
| WO | WO-2006103113 A2 * | 10/2006 | ........... C12Q 1/6883 |
| WO | WO-2007143037 A2 * | 12/2007 | ........... C12Q 1/6886 |
| WO | 2008113773 A2 | 9/2008 | |
| WO | WO-2010006215 A1 * | 1/2010 | ........... C12Q 1/6883 |

OTHER PUBLICATIONS

Massone et al., 17A, a novel non-coding RNA, regulates GABA B alternative splicing and signaling in response to inflammatory stimuli and in Alzheimer disease. Neurobiology of Disease 41 (2011) 308-317.*
Chan et al., GABAB receptor antagonism abolishes the learning impairments in rats with chronic atypical absence seizures. European Journal of Pharmacology 541 (2006) 64-72.*
Chan et al., Thalamic Atrophy in Childhood Absence Epilepsy. Epilepsia, 47(2):399-405, 2006.*
Riban et al.,Gene therapy in epilepsy. Epilepsia. Jan. 2009 ; 50(1): 24-32.*
Collins, "Generation and initial analysis of more than 15,000 full-length human and mouse cDNA sequences", PNAS 99(26), 16899-16903 (2002).
Anonymous, "EM_STD: BC045570", XP055307464, Retrieved from the Internet: URL:http://ibis.internal.epo.org/exam/dbfetch.jsp?id=EM_STD:BC045570, (Feb. 11, 2003).
Genbank, "Homo sapiens Chromosome 16 BAC clone CIT987-SK142A6 complete genomic sequence, complete sequence", accession No. AC002040.1, 47 pages (Oct. 30, 2002).
Genbank, "JP 2008200045-A/732: Guanosine triphosphate-binding protein coupled receptors", accession No. HV321056.1, 124 pages (Jul. 15, 2011).
Genbank, "Method of Screening for the Presence of Genetic Defect Associated with Deep Venous Thrombosis", accession No. DM061108.1, 4 pages (Mar. 30, 2009).
Patent Cooperation Treaty, International Searching Authority, Search Report and Written Opinion for PCT/US2014/021357, 15 pages, dated Aug. 26, 2014.
Strausberg, et al., "Generation and initial analysis of more than 15,000 full-length human and mouse cDNA sequences", Proceedings of National Academy of Sciences 99 (26), 16899-16903 (2002).
Quesada, et al., "Cloning and enzymatic analysis of 22 novel human ubiquitin-specific proteases", Biochemical and Biophysical Research Communications 314, 54-62 (2004).

\* cited by examiner

*Primary Examiner* — Kevin K Hill
*Assistant Examiner* — Arthur S Leonard
(74) *Attorney, Agent, or Firm* — Viksnins Harris Padys Malen LLP (57) ABSTRACT

An isolated promoter sequence comprising a nucleic acid of between 600 and 1700 nucleotides in length having at least 90% identity to SEQ ID NO:1, SEQ ID NO:2, SEQ ID NO:3, SEQ ID NO:4, SEQ ID NO:5, SEQ ID NO:6, or SEQ ID NO:7.

18 Claims, 3 Drawing Sheets
Specification includes a Sequence Listing.

SEQUENCE LISTING

```
<160> NUMBER OF SEQ ID NOS: 7

<210> SEQ ID NO 1
<211> LENGTH: 1622
<212> TYPE: DNA
<213> ORGANISM: Homo sapiens

<400> SEQUENCE: 1
ggaggtcata tactagttga ttttggacta aaggcatccc aaagatgtac tattttttgc    60
tccctgcact attttttttt taatggaacc aacgtttaaa aataggattt ctgccttctc   120
```

```
ttaaaacatc agatgatctg gtaacgctga gctcctgttc tcacatggga acaactggct    180
ggagctgagt ggcagccacc tctttagaaa gatgttaatt tgaagtctgc tatagtcccc    240
atcattcctt atatttcccc caacactgag acccaagtca cttgaaagtc aatatgatga    300
ttcaaacacc aggattcttc actcatttgt gggtttgtga cctgtgatat tgtggattc     360 gtgacctttg gtttagaggt caagtatagg ggttgtaaat aaaacttggg tttgaatcag    420
ataagaactg taccaatctc aaagacggtg aattaaagat taagaaaat attgcatgct     480 tggcataatg tgtggaacac aacagctatt gtaaacaccc agtaggaatg taagctgcaa    540
gagggcaggt agaaaccgtg ctaatttaat ccgctgggga tatgacattt gattctaatt    600
taataggttt aattctttgc aatatcccca gtaactgctg aatgaatgag tgagtgaatg    660
aatgaatgga atgatgaatg atgggagagc ccggaggagt tttaaaggct ggaatgaaaa    720
ggaaagtagt tatgataaca gcgtttcgct gggactccaa ggtgcagcca ggaagaaaag    780
cccgctggga cgtgccaggg tctgtgactg cgctccgctg gcacccagag ggtaggtatc    840
tgcaacgtcc cttgggagcc agacagggct gacttgccca ggacctgtca gggccatgtc    900
caccagctct tgcacggtct ggtaactgac agcatcctga ttcctgcacg ttcccgcctc    960
tgccatctga ccagcaaaga cagagaccca ccccggggat ccaccatcca acgggagccc   1020
agccttttcc tccaagccgg gacggcgccc acactagaca tggcctccct cgggcttcac   1080
gcagcaggac cgcgcccgca gcctccaggc atcgcgtccg gctggagagg cagctaccgt   1140
cccacagtga acatggcggc cgaggcggct tcagcgccgg gcgggcggcg ccgggaggca   1200
cgtcacgtga gcggctcagc tgggcggacc gcgcgcgcgc ccgctggccc cgccggccgc   1260
cgctcgctcg ctggctcggc tgcgctttga ggtgtgtggg gcgtcgagcc cccgggcccg   1320
gtgaggcgcg gcgctgcggg atgcggcggc ggccgtggcg gggccgcggg ccgggcgggc   1380
gggcgcggtg atgagtgtct gcggccgccg ccatgtccaa ggtaacgcgc cctgggtccg   1440
ggccgccggc ggcggcgagc gggaaggaga agcgctcctt cagcaagcgg ctgtttcgga   1500
gcggccgcgc tggcggcggc ggcgcggggg gccccggggc gtccgggccg gccgcgcctt   1560
cctcgccctc ctcgccctcc tctgcacgct cggtgggcag cttcatgagc cgcgttctca   1620
ag                                                                 1622

<210> SEQ ID NO 2
<211> LENGTH: 630
<212> TYPE: DNA
<213> ORGANISM: Homo sapiens

<400> SEQUENCE: 2
tgagaagtga gagcctatga acatggttga cacagaggga caggaatgta tttccagggt     60
cattcattcc tgggaatagt gaactgggac atggggaag tcagtctcct cctgccacag     120
ccacagatta aaataataa tgttaactga tccctaggct aaaataatag tgttaactga     180
tccctaagct aagaaagttc ttttggtaat tcaggtgatg gcagcaggac ccatcttaag    240
gatagactag gtttgcttag ttcgaggtca tatctgtttg ctctcagcca tgtactggaa    300
gaagttgcat cacacagcct ccaggactgc cctcctcctc acagcaatgg ataatgcttc    360
actagccttt gcagataatt ttggatcaga gaaaaacct tgagctgggc caaaaggag      420 gagcttcaac ctgtgtgcaa aatctgggaa cctgacagta taggttgggg gccaggatga    480
ggaaaaagga acgggaaaga cctgcccacc cttctggtaa ggaggccccg tgatcagctc    540
```

| cagccatttg cagtcctggc tatcccagga gcttacataa agggacaatt ggagcctgag | 600 |
| aggtgacagt gctgacacta caaggctcgg | 630 |

<210> SEQ ID NO 3
<211> LENGTH: 1363
<212> TYPE: DNA
<213> ORGANISM: Homo sapiens

<400> SEQUENCE: 3

| ccaagatcag ctcttggagg agtgtagact ttaattccac ctggtggtcc ctacagaacg | 60 |
| gagagtcctt gcccaaaggc acagagaagg atggaacaac aatgtggtgt gtgggggagg | 120 |
| gtctctgcac cttcctgac atcttttctt cgggagatcc tcatagaacc ataatgcttt | 180 |
| gttttgggac cagaagcatc ataagcatca tcatttttcc agcttcatct cctgttactt | 240 |
| tccccttcac ccattctact ccaacctcac actcgctctg tcttgactat tttggacaca | 300 |
| ctcctacccc agcctttgca cttgctattc ctcatgctcg gcgcagttct tccccagaca | 360 |
| tccacacggc ttgctccctc aatttcttca ggctttaaat gttactttct catagaggcc | 420 |
| ttctcttgta tttgagcctc actcttatct cacacttcct attccccttc tccgccttat | 480 |
| ttttctccac cccatgggaga ccctctgaca cattctcccg tttgtctgtc tttccccccac | 540 |
| gagactgcaa actacaggag ggcagagatt tctgcctgtt ctcttggctg tttcatatcc | 600 |
| agcacccaaa tcgatgtatg acacaaaata cgttctcagt acttaatcga attaacgaat | 660 |
| gcatgaatgg caggtattgg acattgtttt gcaaactctt aaagtaaggt gtaaagcatc | 720 |
| ccggtgaggt ggaggttact gccgctgcga ttcccgcgca gcctgaggac tggggggtgg | 780 |
| gggtggggt ctctaattac ctccataatc cccagtagcg gcactttaaa cttcacatca | 840 |
| accctgaggg atgtgtatta ttatccaaat ttagttcaca gctggatgga gaagtggctt | 900 |
| ccggctccac actttggagg aggggagta gagggcaggc ccccatttaa gtacccggga | 960 |
| tggggcacca atgccttcag gcggtaaacc aatttaggaa gacgtggcgg gctttgtggc | 1020 |
| ggctcctcct ctttcggcct gtccgcagtt tttaaaaaac gtgtgtgatg ataaggaatc | 1080 |
| actgtctaca ttagtaattc ccaacttggg tccgaaagtg aacttttgct gaagcgaagt | 1140 |
| agctaaccgc ttccatgtgc aaggcaggtt ccagacttcg gggtgaggag gattaactga | 1200 |
| aggaccccag gggaaccggg tgcgcagtaa ttgatcttgg ggcagaccag ggcttggcgg | 1260 |
| tggcctgtat ctaaagacag cggggtctct gaggcggggc agggggagt tggcattgac | 1320 |
| tggggaggga agagcgatcg ctggtaacag ccattgtgcc ttc | 1363 |

<210> SEQ ID NO 4
<211> LENGTH: 1349
<212> TYPE: DNA
<213> ORGANISM: Homo sapiens

<400> SEQUENCE: 4

| gtgcctgatg tgagatttat tgaaactgga tttgaaaaca attttcctga attcaagtcg | 60 |
| agggtttact ccactattct caattacttt atcaccaggg ttataaaccc aaaggaagtg | 120 |
| agtaacaaca gtgtgatttt attgaggacc catgcaacac tagtctcaga aaggctccag | 180 |
| tgtcatttgt aaaattcaag gttaccatca gcagaggcag tcattcctct ctgcgcttgt | 240 |
| tacctaatgc actaactctc actgtaggta attccattca agacacattt gatgactata | 300 |
| cctacaggtt ttgaagttat tcggatgggg ttttgacact tactagctgt ggggacttag | 360 |

-continued

```
atcaagttac ttaaccttt tgagcttcag ttttatcatt tgtaaaatgg atacaatcct      420
gatgcctttg gaccaagtgg tcacggaaat gaaagagata agtatgaaaa aatccatgct      480
catagtagct gtggtttcca actgcgtgat aaaactttaa aatctgcatt caaataagaa      540
caactatgtc gacgtaaggt tacaagctaa ctattcttgg taagtactgt tctttattct      600
agaggacatc actttacagt ttggtgctaa atgctctttt atgaatttaa ggtgccagta      660
gctgtctact tgaacggcat gcttaatctg gaacgccatg tcgaccttca tcccccagtt      720
cttctcccc aaattaaaaa cacaaataca cacacgcc cctacttagt tcctaaaact        780
caagggcacg cgcacacacc tactatttc ctaaaattca agctcgcacc aaggagatcc      840
acaaggatag gcagggtggt ggaggtcact gggcagcgcc tccggatccc cgaaaggggg     900
gcggggtcaa aactcagatc tcgagctccc gaaaggggc ggggttaaaa ctctcagatc      960
tcattccgcc tccctctgtc gtcgccctt cccaattctc gcgagacctc aaggagcaca     1020
gcttctgcgc accgcacgat actgggagtc caggcgccaa gggaggggga agggaaaagg    1080
ggaaacggtg caaacggcgt ggccgccatc ttgcttgtgc ccccgcttcg cgcgcgctcc    1140
gttctccgtg acgcacactt ccccctcccc tccgccgcgc ctgggcctct gcattgcccg    1200
actccgtagg agcgcggggg cggctcctgc tcttcctgga ctcctgagca gaggtgtgtg    1260
agtgtgcggg agtttctgtg cgagggtgat agggaagcgg cggcgggggg aggggcagcg    1320
cttcccgcct tcgccagaga cctcacttc                                     1349
```

<210> SEQ ID NO 5
<211> LENGTH: 1059
<212> TYPE: DNA
<213> ORGANISM: Homo sapiens

<400> SEQUENCE: 5

```
cttttgggag atttacgggg ctagaacagg agaccacccc cgttttttg tttgtttgtt       60
ttgtttttg ttttggtga acgtagtct cgctctgtca cccaggctgg agtgcagtgg        120
cgcgatctcg gtcactgcaa catccgcctc cagggttcaa gcgattcttc tgcctctgcc      180
tccagagtag ctgggattac aggcgcgcat caccacaccc ggctaatttt tgtattttta      240
gtagagacgg ggtttcacca tgttggtcag gctgatctcg aactcctgac ctcaagtgat      300
ccgctctcct cagcctccca aagtgctggg attacaggcg taagccactg agccggcca      360
ggagacctct ttaagaagac tcgagatgtc gacaatccca gtggatggat accaacttta      420
aaaagaaaag ttcaaaaggc ctatgtgccc attagctggg aggggccaag aaatatggga      480
gtcccttata gtgggggtaa aacgcgggt aaagctaggt gggcggaaca gcagcttctg      540
ggggagacaa gcggcaaaga ggctcacgac cgactagggg cgaccaaggc tgatagccgt      600
tggggccgtt gggcgccggg agctggcgcc ccgccctctc tcctctcccc caccctccgc      660
acctcccacc accctcggtg tccctgcgc gtgcgcgtga agacaccggt tgccaaacat      720
tgcatcatcc ccgcccccct ttcctcccct cccccccgc tacactcccc tccgcgcgcg      780
cgcatgactc acccacctcc tccgtgaagc ctcgtgaccc aaagccactt ccgggtccga      840
cactacgtcg accccctagc gagagggagc gacggggcg gtgccgcggg gctcctgagt      900
ggcggatgcg agggacgggg cggggccaat gccggcgtgc cactttctga ttggtaggtt      960
ttgggggtccc gcccctgaga ggagggcaag gccatggtaa aagattacag ccaggcgctc    1020
ccgaggtcag agacttaagt ctaaggcact gagcgtatc                           1059
```

```
<210> SEQ ID NO 6
<211> LENGTH: 524
<212> TYPE: DNA
<213> ORGANISM: Homo sapiens

<400> SEQUENCE: 6
taataacaac atatctgaaa aagacgcttt aaaatcccat ttatgaaagc ataaaaatag      60
ttagaaataa atttaaccat aaaggtgaaa tatttgtata ccgataacta taaacctttg     120
ataaaaaaag ttgaagaaga cacatataaa tagaataata ttctgtgttc atgaatcaaa     180
aaatttaaca atgttaaaat gtctgtatta accaaagcaa tatacaaatt caatgcaatt     240
tctatcaaaa tttcaaggat atgcatcaca gaaatagaaa aaaaattctt gaaattcata     300
tggaaccaca gacacataaa aacagaatag gcaaaggaac aatgagaaag caaaacaaag     360
cttgaggcat cacacttcct aagttaaaat tatattgcaa agctacagta atcaaaaaca     420
gtatacaaat ggcatgaaaa cgaaaatgtg gaccaacgga acagaatata gagagccaga     480
aacttaacta attttcaaca agggtaccaa caggacaccc tgaa                     524

<210> SEQ ID NO 7
<211> LENGTH: 952
<212> TYPE: DNA
<213> ORGANISM: Homo sapiens

<400> SEQUENCE: 7
atttccacca gcaacacaca agggttccag tttctccaca tcttcaccaa cacttgtggt      60
tttgcttttt ggtaatagcc atgctaatgg gtgtgaacaa gaagtgcttt aagcatctcc     120
taaagcggaa gaaactgagg cccagagaag ggaagaatca cacgagagat tgaggtcaca     180
agcaagtcag tgatagagca ggacctggaa gctggatccc ctaaccccag cctagttctt     240
gctactaaaa cccaaaatcc agtttccatt gctatatgtc agagggtgca cagccatggc     300
cacaggccag atacagactt taagtttatt tggtttgatc cttactttct ttttttttta     360
attcaaaata gtatcaacat ttaaaaatta ggggatttta tattttaaaa gtctaaattt     420
ctgatttctc ccctcaaaaa tcagaaggtc tggtaaccct tgacccacat tctaactcag     480
caaccaacta ttactgtctt ttgttttgtt ttgttctgtt gagacaaggt cttgttctgt     540
cacccaggct ggagtacggt ggcgtgatca cggctcactg cagtcttgaa ctcctgggct     600
caagcaagcc ccccgtcttg gcctcccaaa gctctgggat tacaggtgtg agcccacgcc     660
cagccctatc attctgtaat atccttccac acaggctagt tcacacactg gctggtcctg     720
gtaacactgg agtttgcagc cctttgcttt tcacatccat agatattcct cattctgagt     780
gtcagtagac acatagttac gtgtaacatc ataggcaggt tccatacttc tttcctcttt     840
cctttactct atattgtctt tgaatatctt agctatttcc tcaccataaa agtgaaataa     900
tgttgcaaat aaatagtgca aaatattaac aaagacacaa ttgaatagcc tg             952
```

PROMOTER COMPOSITIONS

RELATED APPLICATION

This application claims priority to U.S. Provisional Patent Application No. 61/794,818 filed Mar. 15, 2013, the entirety of which is incorporated herein by reference.

BACKGROUND

Current approaches to gene therapy for neurodegenerative diseases lack the ability to turn on and shut off expression of the delivered therapeutic gene. In addition, current approaches lack the ability to dose the expression of the therapeutic gene after delivery. There is a current need for regulatable promoters.

SUMMARY

In certain embodiments, the present invention provides an isolated promoter sequence comprising (or consisting of) a nucleic acid of between 500 and 1700 nucleotides in length having at least 90% identity to SEQ ID NO:1, SEQ ID NO:2, SEQ ID NO:3, SEQ ID NO:4, SEQ ID NO:5, SEQ ID NO:6, or SEQ ID NO:7. In certain embodiments, the promoter has 90%, 91%, 92%, 93%, 94%, 95%, 96%, 97%, 98%, 99% or 100% identity to SEQ ID NO:1, SEQ ID NO:2, SEQ ID NO:3, SEQ ID NO:4, SEQ ID NO:5, SEQ ID NO:6, or SEQ ID NO:7.

In certain embodiments, the present invention provides an expression cassette comprising the promoter described above that is functional in a transformed cell operably linked to a preselected DNA segment encoding a protein or RNA transcript. In certain embodiments, the preselected DNA segment comprises a selectable marker gene or a reporter gene. In certain embodiments, the preselected DNA segment encodes a therapeutic composition. In certain embodiments, the therapeutic composition is an RNAi molecule.

In certain embodiments, the present invention provides a vector comprising the expression cassette described above. In certain embodiments, the vector is an adeno-associated virus (AAV) vector.

In certain embodiments, the present invention provides a transformed cell comprising the expression cassette described above, or the vector described above. In certain embodiments, the host cell is a eukaryotic cell. In certain embodiments, the eukaryotic cell is an animal cell (e.g. a mammalian cell, such as a human cell).

In certain embodiments, the present invention provides a method for producing transformed cells comprising the steps of (i) introducing into cells a recombinant DNA which comprises a promoter described above operably linked to a DNA segment so as to yield transformed cells, and (ii) identifying or selecting a transformed cell line. In certain embodiments, the recombinant DNA is expressed so as to impart a phenotypic characteristic to the transformed cells. In certain embodiments, the transformed cells exhibit significantly increased expression of a reporter gene when introduced into the cells derived from Huntington's disease patients as compared to cells derived from control individuals.

In certain embodiments, the present invention provides transformed cell made by the method described above.

In certain embodiments, the present invention provides a transformed cell comprising the isolated promoter described above.

In certain embodiments, the present invention provides transformed cell comprising the expression cassette described above.

In certain embodiments, the present invention provides method of treating a neurodegenerative disease in a mammal comprising administering (a) the vector described above, or (b) the transformed cell described above.

DETAILED DESCRIPTION

The present invention provides the use of gene promoter sequences that can activate, enhance or repress the expression of a genetic sequence at the onset of or during the pathological progression of a neurodegenerative disorder. This invention is directly applicable to the field of gene therapy. It has potential commercial value as a tool in the development of regulated gene therapy approaches to neurodegenerative diseases. This invention provides a means on which to dose or regulate the expression of therapeutic genes during the course of disease based on the state or rate of progression of the neurodegenerative disease. For example, during disease progression, the gene promoter sequences can activate the expression of a therapeutic gene. If the therapy halts the progression of disease, activity of the gene promoter sequence would wane, resulting in reduced/limited therapeutic gene expression. This disease-regulated dynamic approach to therapeutic gene expression is unique and needed in the gene therapy field.

The invention is applicable to the field of gene therapy. It satisfies a need for the regulation and/or dosing of therapeutic genes after delivery into the brain. Gene expression analyses have shown that at the onset and/or during the course of neurodegenerative disease progression, a number of gene promoter sequences act to "turn-on," enhance, repress or "shut-off" the expression of genes. The present inventors have identified and cloned gene promoter sequences that activate and/or enhance gene expression during neurodegenerative disease progression in cell and animal models of neurodegenerative disease. These gene promoter sequences can also activate and/or enhance the expression of a reporter gene during neurodegenerative disease progression in models of neurodegenerative disease. This approach is unique and different from the current systems used to artificially regulate therapeutic gene expression in that it relies on neurodegenerative disease related molecular events to modulate the expression of the therapeutic genes. These events, and thus the activity of the specific gene promoter sequences, are controlled/induced by intracellular and/or extracellular signals that are dependent on the onset and/or progression of disease.

The present inventors have identified, cloned and tested the activity of seven different gene promoter sequences in tissue cultured cells obtained from control individuals or individuals who carry the Huntington's disease (i.e., neurodegenerative disease) gene mutation. The experiments demonstrate that these gene promoter sequences can drive significantly increased expression of a reporter gene when introduced into the cells derived from Huntington's disease patients as compared to cells derived from control individuals. Moreover, introduction of an artificial stressor such as a proteasome inhibitor or a pro-inflammatory stimulus results in increased activity from the gene promoter sequences as measured by the expression of endogenously controlled transcripts or a reporter gene in cultured cells. In addition, we have detected in the brains of mouse models of Huntington's' disease (i.e., neurodegenerative disease) a disease progression-dependent increase in the activity of these gene promoter sequences as measured by quantitative PCR analysis of the endogenous regulated gene transcripts.

Promoter Sequences

In certain embodiments, the present provides the following promoter sequences that activate and/or enhance gene expression: ubiquitin specific peptidase 31 (USP31, SEQ ID NO:1), gamma-FBG (SEQ ID NO:2), H2A histone family, member Y (H2AFY, SEQ ID NO:3), Nuclear transcription factor Y, gamma (NYFC, SEQ ID NO:4), DNA-damage-inducible transcript 3 (CHOP, SEQ ID NO:5), Non-coding 38A RNA (38A locus, SEQ ID NO:6), and Non-coding 17A RNA (17A, SEQ ID NO:7).

GeneID: USP31

(SEQ ID NO: 1)
GGAGGTCATATACTAGTTGATTTTGGACtaaaggcatcccaaagatgtac tattttttgctccctgcactattttttttttatttaatggaaccaacgtt taaaaataggatttctgccttctcttaaaacatcagatgatctggtaacg ctgagctcctgttctcacatgggaacaactggctggagctgagtggcagc cacctctttagaaagatgttaatttgaagtctgctatagtccccatcatt ccttatatttccccaacactgagacccaagtcacttgaaagtcaatatg atgattcaaacaccaggattcttcactcatttgtgggtttgtgacctgtg atatttgtggattcgtgacctttggtttagaggtcaagtatagggggttgt aaataaaacttgggtttgaatcagataagaactgtaccaatctcaaagac ggtgaattaaagattaaagaaaatattgcatgatggcataatgtgtggaa cacaacagctattgtaaacacccagtaggaatgtaagctgcaagagggca ggtagaaaccgtgctaatttaatccgctggggatatgacatttgattcta atttaataggtttaattattgcaatatccccagtaactgctgaatgaatg agtgagtgaatgaatgaatggaatgatgaatgatgggagagcccggagga gttttaaaggctggaatgaaaaggaaagtagttatgataacagcgtttcg ctgggactccaaggtgcagccaggaagaaaagcccgctgggacgtgccag ggtctgtgactgcgctccgctggcacccagagggtaggtatctgcaacgt cccttgggagccagacagggctgacttgcccaggacctgtcagggccatg tccaccagctcttgcacggtctggtaactgacagcatcctgattcctgca cgttcccgcctctgccatctgaccagcaaagacagagacccaccccgggg atccaccatccaacgggagcccagccttttcctccaagccgggacggcgc ccacactagacatggcctccctcgggatcacgcagcaggaccgcgccgc agcctccaggcatcgcgtccggctggagaggcagctaccgtcccacagtg aacatggcggccgaggcggcttcagcgccgggcgggcggcgccgggaggc acgtcacgtgagcggctcagctgggcggaccgcgcgcgcgcccgctggcc ccgccggccgccgctcgctcgctggctcggctgcgctttgaggtgtgtgg ggcgtcgagccccgggcccggtgaggcgcggcgctgcgggatgcggcgg cggccgtggcggggccgcgggccgggcgggcgggcgcggtgatgagtgtc tgcggccgccgccatgtccaaggtaacgcgcctgggtccgggccgccgg cggcggcgagcgggaaggagaagcgctccttcagcaagcggctgtttcgg agcggccgcgctggcggcggcggcgcgggggggccccggggcgtccgggcc ggccgcgccttcctcgccctcctcgccctcctctgcacgctcggtgggcA

GCTTCATGAGCCGCGTTCTCAAG

Gene ID: gamma-FBG (SEQ ID NO: 2)
TGAGAAGTGAGAGCCTATGAACATGGttgacacagagggacaggaatgta tttccagggtcattcattcctgggaatagtgaactgggacatgggggaag tcagtctcctcctgccacagccacagattaaaaataataatgttaactga tccctaggctaaaataatagtgttaactgatccctaagctaagaaagttc ttttggtaattcaggtgatggcagcaggacccatcttaaggatagactag gtttgcttagttcgaggtcatatctgtttgctctcagccatgtactggaa gaagttgcatcacacagcctccaggactgccctcctcctcacagcaatgg ataatgcttcactagccttttgcagataattaggatcagagaaaaaacctt gagctgggccaaaaaggaggagcttcaacctgtgtgcaaaatctgggaac ctgacagtataggttggggcaggatgaggaaaaaggaacgggaaagac ctgcccaccatctggtaaggaggcccgtgatcagctccagccatttgca gtcctggctatcccaggagcttacataaagggacaattggagcctgagag gtGACAGTGCTGACACTACAAGGCTCGG Gene ID: H2AFY (SEQ ID NO: 3)
CCAAGATCAGCTCTTGGAGGAGTGtagactttaattccacctggtggtcc ctacagaacggagagtccttgcccaaaggcacagagaaggatggaacaac aatgtggtgtgtgggggagggtctctgcacctttcctgacatcttacttc gggagatcctcatagaaccataatgctttgttttgggaccagaagcatca taagcatcatcattttccagcttcatctcctgttacttcccttcacc cattctactccaacctcacactcgctctgtcttgactattttggacacac tcctacccagcattgcacttgctattcctcatgctcggcgcagttcttc cccagacatccacacggcttgctccctcaattcttcaggctttaaatgt tactttctcatagaggccttctatgtatttgagcctcactatatctcaca cttcctattcccttctccgccttatttttctccacccatggagaccct ctgacacattctcccgtttgtctgtctttcccccacgagactgcaaacta caggagggcagagatttctgcctgttctcttggctgtttcatatccagca cccaaatcgatgtatgacacaaaatacgttctcagtacttaatcgaatta acgaatgcatgaatggcaggtattggacattgttttgcaaactcttaaag taaggtgtaaagcatcccggtgaggtggaggttactgccgctgcgattcc cgcgcagcctgaggactggggggtgggggtggggtctctaattacctcc -continued

```
ataatcccagtagcggcacttttaaacttcacatcaaccctgagggatgt
gtattattatccaaatttagttcacagctggatggagaagtggcttccgg
ctccacactttggagggaggggagtagagggcaggccccccatttaagtac
ccggatggggcaccaatgccttcaggcggtaaaccaatttaggaagacg
tggcgggctttgtggcggctcctcctctttcggcctgtccgcagttttta
aaaaacgtgtgtgatgataaggaatcactgtctacattagtaattcccaa
cttgggtccgaaagtgaacttttgctgaagcgaagtagctaaccgcttcc
atgtgcaaggcaggttccagacttcggggtgaggaggattaactgaagga
ccccaggggaaccgggtgcgcagtaattgatcttggggcagaccagggct
tggcggtggcctgtatctaaagacagcggggtctctgaggcggggcaggg
gggagttggcattgactggggagggaagagcgatcGCTGGTAACAGCCAT
TGTGCCTTC
```

Gene ID: NYFC
(SEQ ID NO: 4)
```
GTGCCTGATGTGAGATTTATTGAAACTGGatttgaaaacaattttcctga
attcaagtcgagggtttactccactattctcaattactttatcaccaggg
ttataaacccaaaggaagtgagtaacaacagtgtgattttattgaggacc
catgcaacactagtctcagaaaggctccagtgtcatttgtaaaattcaag
gttaccatcagcagaggcagtcattcctctctgcgcttgttacctaatgc
actaactctcactgtaggtaattccattcaagacacatttgatgactata
cctacaggttttgaagttattcggatgggttttgacacttactagctgt
ggggacttagatcaagttacttaaccttttttgagcttcagttttatcatt
tgtaaaatggatacaatcctgatgcctttggaccaagtggtcacggaaat
gaaagagataagtatgaaaaaatccatgctcatagtagctgtggtttcca
actgcgtgataaaactttaaaatctgcattcaaataagaacaactatgtc
gacgtaaggttacaagctaactattcttggtaagtactgttcttttattct
agaggacatcactttacagtttggtgctaaatgctatttatgaatttaag
gtgccagtagctgtctacttgaacggcatgcttaatctggaacgccatgt
cgaccttcatccccagttctttctcccaaattaaaaacacaaatacac
acacacgcccctacttagttcctaaaactcaagggcacgcgcacacacct
acttatttcctaaaattcaagctcgcaccaaggagatccacaaggatagg
cagggtggtggaggtcactgggcagcgcctccggatccccgaaaggggg
cggggtcaaaactcagatctcgagctcccgaaaggggggggggttaaaac
tctcagatctcattccgcctccctctgtcgtcgcccatcccaattctcgc
gagacctcaaggagcacagcttctgcgcaccgcacgatactgggagtcca
ggcgccaagggaggggaaggaaagggaaacggtgcaaacggcgtgg
ccgccatcttgcttgtgccccgcttcgcgcgcgctccgttctccgtgac
gcacacttcccccctcccctccgccgcgcgcctgggcctctgcattgcccgac
tccgtaggagcgcggggcggctcctgctcttcctggactcctgagcaga
ggtgtgtgagtgtgcggagttctcgtgcgagggtgatagggaagcggcg
gcggggggaggggcagcgcttccCGCCTTCGCCAGAGACCTCACTTC
```

Gene ID: CHOP
(SEQ ID NO: 5)
```
CTTTTGGGAGATtTACGGGGCTAGAACAGGAGACCACCCcgttttttta
ttgtttgtttgttttgttttttgttttttggtgaaacgtagtctcgctctg
tcacccaggctggagtgcagtggcgcgatctcggtcactgcaacatccgc
ctccagggttcaagcgattcttctgcctctgcctccagagtagctgggat
tacaggcgcgcatcaccacacccggctaattttttgtatttttagtagaga
cggggtttcaccatgttggtcaggctgatctcgaactcctgacctcaagt
gatccgctctcctcagcctcccaaagtgctgggattacaggcgtaagcca
ctgagcccggccaggagacctcttttaagaagactcgagatgtcgacaatc
ccagtggatggataccaacttttaaaaagaaaagttcaaaaggcctatgtg
cccattagctgggagggggccaagaaatatgggagtcccttatagtggggg
taaaacggcgggtaaagctaggtgggcggaacagcagcttctgggggaga
caagcggcaaagaggctcacgaccgactaggggcgaccaaggctgatagc
cgttgggccgttgggcgccgggagctggcgccccgccctctctcctctc
ccccaccctccgcacctcccaccaccctcggtgtccctgcgcgtgcgcg
tgcagacaccggttgccaaacattgcatcatccccgcccccattcctccc
ctccccccccgctacactcccctccgcgcgcgcgcatgactcacccacct
cctccgtgaagcctcgtgacccaaagccacttccgggtccgacactacgt
cgaccccctagcgagagggagcgacggggcggtgccgcggggctcctga
gtggcggatgcgagggacgggcggggccaatgccggcgtgccactttct
gattggtaggttttgggtcccgcccctgagaggagggcaaggccatggt
aaaagattacagccaggcgctcCCGAGGTCAGAGACTTAAGTCTAAGgca
CTGAGCGTATC
```

Gene ID: 38A locus
(SEQ ID NO: 6)
```
TAATAACAACATATCTGAAAAAGACGCttttaaaatcccatttatgaaagc
ataaaaatagttagaaataaatttaaccataaaggtgaaatatagtatac
cgataactataaaccctttgataaaaaaagttgaagaagAcacatataaat
agaataatattctgtgttcatgaatcaaaaaatttaacaatgttaaaatg
tctgtattaaccaaagcaatatacaaattcaatgcaattctatcaaaat
ttcaaggatatgcatcacagaaatagaaaaaaaattcttgaaattcatat
ggaaccacagacacataaaaacagaataggcaaaggaacaatgagaaagc
aaaacaaagcttgaggcatcacacttcctaagttaaaattatattgcaaa
gctacagtaatcaaaaacagtatacaaatggcatgaaaacgaaaatgtgg
accaacggaacagaatatagagagccagaaacttaactaaTTTTcaacaa
gGGTACCAACAGGACACCCTGAA
```

Gene ID: 17A locus
(SEQ ID NO: 7)
```
ATTTCCACCAGCAACACACAAGGGTTCCAGTTTCTTCCACATCTTCACCAA
CACTTGTGGTTTTGCTTTTTGGTAATAGCCATGCTAATGGGTGTGAACAA
GAAGTGCTTTAAGCATCTCCTAAAGCGGAAGAAACTGAGGCCCAGAGAAG
GGAAGAATCACACGAGAGATTGAGGTCACAAGCAAGTCAGTGATAGAGCA
GGACCTGGAAGCTGGATCCCCTAACCCCAGCCTAGTTCTTGCTACTAAAA
```

-continued
```
CCCAAAATCCAGTTTCCATTGCTATATGTCAGAGGGTGCACAGCCATGGC

CACAGGCCAGATACAGACTTTAAGTTTATTTGGTTTGATCCTTACTTTCT

TTTTTTTTTAATTCAAAATAGTATCAACATTTAAAAATTAGGGGATTTTA

TATTTTAAAAGTCTAAATTTCTGATTTCTCCCCTCAAAAATCAGAAGGTC

TGGTAACCCTTGACCCACATTCTAACTCAGCAACCAACTATTACTGTCTT

TTGTTTTGTTTTGTTCTGTTGAGACAAGGTCTTGTTCTGTCACCCAGGCT

GGAGTACGGTGGCGTGATCACGGCTCACTGCAGTCTTGAACTCCTGGGCT

CAAGCAAGCCCCCGTCTTGGCCTCCCAAAGCTCTGGGATTACAGGTGTG

AGCCCACGCCCAGCCCTATCATTCTGTAATATCCTTCCACACAGGCTAGT

TCACACACTGGCTGGTCCTGGTAACACTGGAGTTTGCAGCCCTTTGCTTT

TCACATCCATAGATATTCCTCATTCTGAGTGTCAGTAGACACATAGTTAC

GTGTAACATCATAGGCAGGTTCCATACTTCTTTCCTCTTTCCTTTACTCT

ATATTGTCTTTGAATATCTTAGCTATTTCCTCACCATAAAAGTGAAATAA

TGTTGCAAATAAATAGTGCAAAATATTAACAAAGACACAATTGAATAGCC

TG
```

"Promoter" refers to a nucleotide sequence, usually upstream (5') to its coding sequence, that controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

As used herein, "biologically active" means that the promoter has at least about 0.1%, 10%, 25%, 50%, 75%, 80%, 85%, even 90% or more, e.g. 91%, 92%, 93%, 94%, 95%, 96%, 97%, 98%, 99% or 100% of the activity of the CCT promoter comprising SEQ ID NO:1 or SEQ ID NO:2. The activity of a promoter can be determined by methods well known to the art. For example, see Sambrook et al., Molecular Cloning: A Laboratory Manual (1989). Promoters of the present invention that are not identical to SEQ ID NO:1 or SEQ ID NO:2, but retain comparable biological activity, are called variant promoters. The nucleotide sequences of the invention include both naturally occurring sequences as well as recombinant forms.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

Vectors and Expression Cassettes

In certain embodiments, the present invention provides vectors and expression cassettes containing the promoters described above.

Vectors

A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

The selection and optimization of a particular expression vector for expressing a specific therapeutic composition (e.g., a protein) in a cell can be accomplished by obtaining the nucleic acid sequence encoding the protein, possibly with one or more appropriate control regions (e.g., promoter, insertion sequence); preparing a vector construct comprising the vector into which is inserted the nucleic acid sequence encoding the protein; transfecting or transducing cultured cells in vitro with the vector construct; and determining whether the protein is present in the cultured cells.

Vectors for cell gene therapy include viruses, such as replication-deficient viruses. Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are well known in the art.

An advantage of using retroviruses for gene therapy is that the viruses insert the nucleic acid sequence encoding the target protein into the host cell genome, thereby permitting the nucleic acid sequence encoding the target protein to be passed on to the progeny of the cell when it divides. Promoter sequences in the LTR region have can enhance expression of an inserted coding sequence in a variety of cell types.

Another viral candidate useful as an expression vector for transformation of cells is an adenovirus (Ad), which is a double-stranded DNA virus. The adenovirus is infective in a wide range of cell types, including, for example, muscle and endothelial cells. Adenoviruses are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Examples of appropriate vectors include DNA viruses (e.g., adenoviruses), lentiviral, adeno-associated viral (AAV), poliovirus, HSV, or murine Moloney-based viral vectors, viral vectors derived from Harvey Sarcoma virus, ROUS Sarcoma virus, MPSV or hybrid transposon based vectors. In one embodiment, the vector is AAV. AAV is a small nonpathogenic virus of the parvoviridae family. AAV is distinct from the other members of this family by its dependence upon a helper virus for replication. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

To-date many serologically distinct AAVs have been identified and have been isolated from humans or primates. For example, the genome of AAV2 is 4680 nucleotides in length and contains two open reading frames (ORFs). The left ORF encodes the non-structural Rep proteins, Rep 40, Rep 52, Rep 68 and Rep 78, which are involved in regulation of replication and transcription in addition to the production of single-stranded progeny genomes. Rep68/78 has also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats (ITR) which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs which occurs in a site- and strand-specific manner. AAV vectors have several features that make it an attractive vector for gene transfer, such as possessing a broad host range, are capable of transduce both dividing and non-dividing cells in vitro and in vivo, and are capable of maintaining high levels of expression of transduced genes.

In certain embodiments, the viral vector is an AAV vector. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight known serotypes of primate AAVs, AAV1 to AAV8. For example, serotype AAV9 is used to refer to an AAV which contains capsid proteins encoded from the cap gene of AAV9 and a genome containing 5' and 3' ITR sequences from the same AAV9 serotype. In certain embodiments, the AAV vector is AAV9.

The abbreviation "rAAV" refers to recombinant adeno-associated virus, also referred to as a recombinant AAV vector (or "rAAV vector"). In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus.

The nucleotide sequences of AAV ITR regions are known. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector.

Nucleic acids encoding therapeutic compositions can be engineered into an AAV vector using standard ligation techniques, such as those described in Sambrook and Russell, Molecular Cloning: A Laboratory Manual, Cold Spring Harbor Laboratory Press Cold Spring Harbor, N.Y. (2001). For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

In certain embodiments, the adeno-associated virus packages a full-length genome, i.e., one that is approximately the same size as the native genome, and is not too big or too small. In certain embodiments the AAV is not a self-complementary AAV vector.

The viral vector further includes a promoter for controlling transcription of the heterologous gene. The promoter may be an inducible promoter for controlling transcription of the therapeutic composition. The expression system is suitable for administration to the mammalian recipient.

In certain embodiments, viral particles are administered. Viral particles are heat stable, resistant to solvents, detergents, changes in pH, temperature, and can be concentrated on CsCl gradients. AAV is not associated with any pathogenic event, and transduction with AAV vectors has not been found to induce any lasting negative effects on cell growth or differentiation. The ITRs have been shown to be the only cis elements required for packaging allowing for complete gutting of viral genes to create vector systems.

In certain embodiments, the present invention provides a vector containing an expression cassette comprising a promoter operably linked to a target sequence. "Expression cassette" as used herein means a nucleic acid sequence capable of directing expression of a particular nucleotide sequence in an appropriate host cell, which includes a promoter operably linked to the nucleotide sequence of interest that may be operably linked to termination signals. The coding region usually codes for a functional RNA of interest, for example an RNAi molecule. The expression cassette including the nucleotide sequence of interest may be chimeric.

Certain embodiments of the present invention provide a vector that encodes a target molecule, such as an isolated RNAi molecule. As used herein the term "encoded by" is used in a broad sense, similar to the term "comprising" in patent terminology. RNAi molecules include siRNAs, shRNAs and other small RNAs that can or are capable of modulating the expression of a target gene, for example via RNA interference. Such small RNAs include without limitation, shRNAs and miroRNAs (miRNAs).

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Nucleic acid is "operably linked" when it is placed into a functional relationship with another nucleic acid sequence. Generally, "operably linked" means that the DNA sequences being linked are contiguous. However, enhancers do not have to be contiguous. Linking is accomplished by ligation at convenient restriction sites. If such sites do not exist, the synthetic oligonucleotide adaptors or linkers are used in accordance with conventional practice. Additionally, multiple copies of the nucleic acid encoding enzymes may be linked together in the expression vector. Such multiple nucleic acids may be separated by linkers.

"Expression" refers to the transcription and/or translation of an endogenous gene or a transgene in cells. For example, in the case of antisense constructs, expression may refer to the transcription of the antisense DNA only. In addition, expression refers to the transcription and stable accumulation of sense (mRNA) or functional RNA. Expression may also refer to the production of protein.

"Expression cassette" as used herein means a DNA sequence capable of directing expression of a particular nucleotide sequence in an appropriate host cell, comprising a promoter operably linked to the nucleotide sequence of interest that is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Such expression cassettes will comprise the transcriptional initiation region linked to a nucleotide sequence of interest. Such an expression cassette may be provided with a plurality of restriction sites for insertion of the gene of interest to be under the transcriptional regulation of the regulatory regions. The expression cassette may additionally contain selectable marker genes.

The present disclosure also provides a mammalian cell containing a vector described herein. The cell may be human, and may be from brain, spleen, kidney, lung, heart, or liver. The cell type may be a stem or progenitor cell population.

Nucleic Acids Encoding Therapeutic Composition

The present invention provides a method of administering a therapeutic composition. In certain embodiments, the therapeutic composition is a transgene, which is a gene encoding a polypeptide that is foreign to the retrovirus from which the vector is primarily derived and has a useful biological activity in the organism into which it is administered (e.g., a therapeutic gene). As used herein, the term "therapeutic gene" refers to a gene whose expression is desired in a cell to provide a therapeutic effect, e.g., to treat a disease.

Methods of Use

The present disclosure provides a method of treating a neurodegenerative disease such as a genetic disease, such as Huntington's disease, ALS, hereditary spastic hemiplegia, primary lateral sclerosis, spinal muscular atrophy, Kennedy's disease, Alzheimer's disease, a polyglutamine repeat disease, or focal exposure such as Parkinson's disease by administering a vector containing the isolated promoters described above.

Certain aspects of the disclosure relate to polynucleotides, polypeptides, vectors, and genetically engineered cells (modified in vivo), and the use of them. In particular, the disclosure relates to a method for gene or protein therapy that is capable of both systemic delivery of a therapeutically effective dose of the therapeutic agent.

The invention will now be illustrated by the following non-limiting Example.

Example 1

Figure 1:
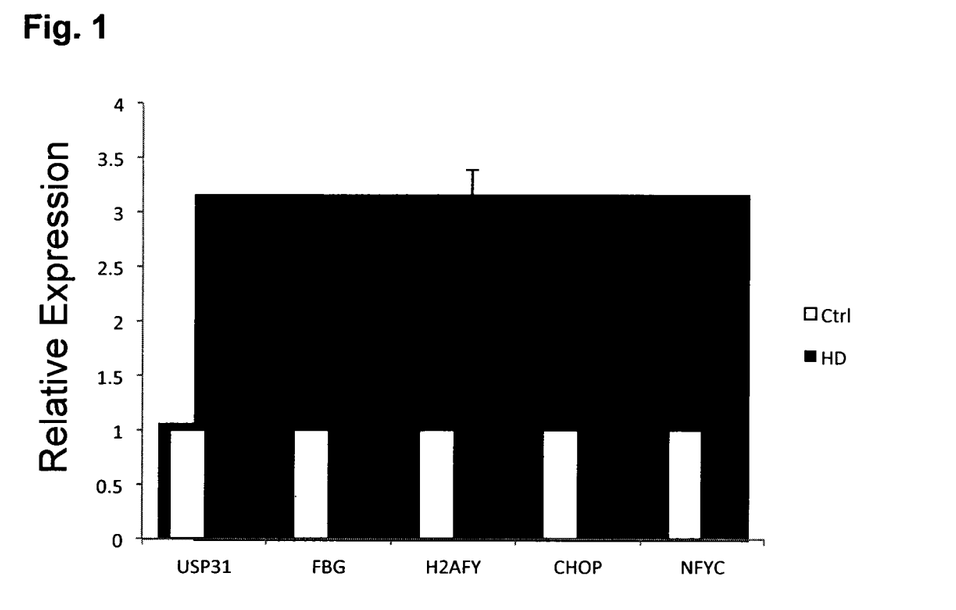
FIG. 1. Expression analysis for five of the promoters demonstrates upregulation of their endogenous transcripts in Huntington's disease postmortem brain patient material when compared to healthy control individuals.

For this experiment, post-mortem human brain tissue obtained from 6 different Huntington's disease patients or 5 control healthy individuals were used to analyze the activity of the 5 different polymerase 2 promoters. RNA was extracted and subjected to quantitative PCR in order to measure the amount of endogenous RNA transcript produced by these promoters. We found significant upregulation for all five promoters in the brains of Huntington's disease patients when compared to the healthy individuals. FIG. 1.

Figure 2A:
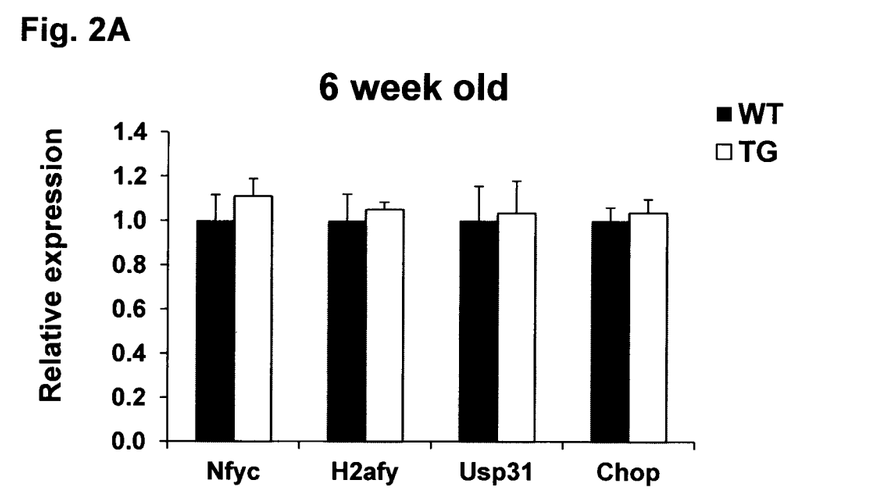
FIGS. 2A-2C. Upregulation of the endogenous transcripts in the brain of Huntington's disease mice at 6 weeks (FIG. 2A), 11 weeks (FIG. 2B) and 19 weeks ((FIG. 2C).
Figure 2B:
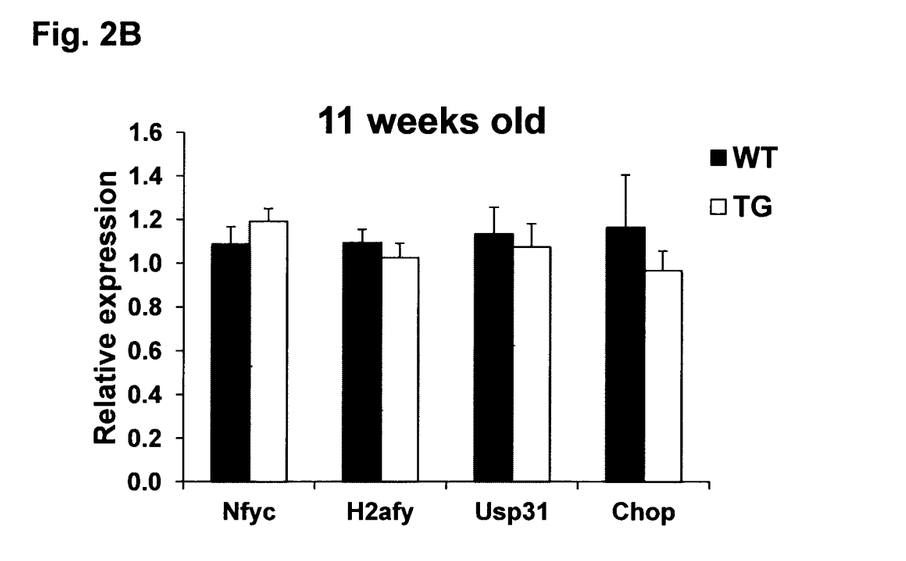
Figure 2C:
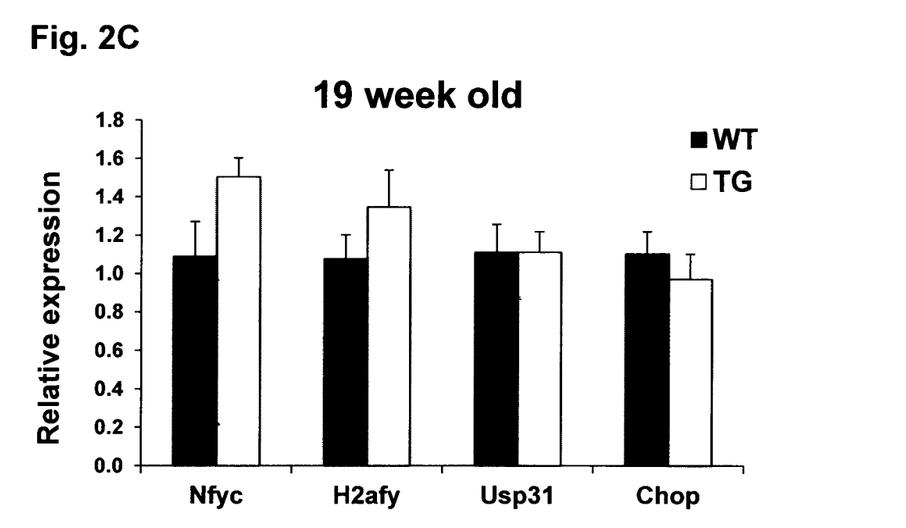

Wild type and HD mice were sacrificed at 6 and 11 weeks (pre-symptomatic) and at 19 weeks (symptomatic) old. Total RNA was isolated from striatum samples and expression of mouse Nfyc, H2afy, Usp31 and Chop genes were determined by using real time Q-PCR. At 6 and 11 weeks of age none of the genes were up-regulated, whereas at 19 week of age the expression of Nfyc and H2afy was significantly upregulated. Number of mice tested are 4 per group. FIGS. 2A-2C.

Figure 3:
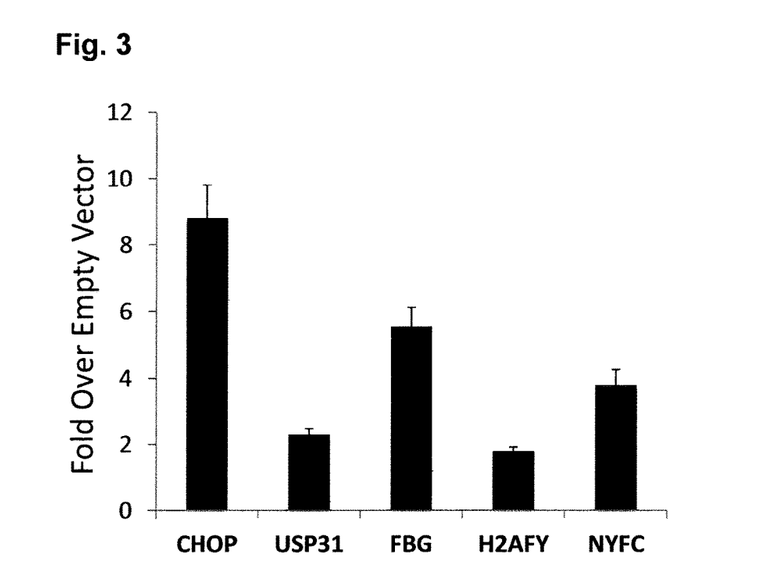
FIG. 3. Activity of the cloned, gene promoter sequences.

Each of the gene promoter sequences were cloned upstream of a reporter gene encoding for Firefly Luciferase. These constructs were transiently expressed in human cultured cells in order to validate their transcriptional activity at basal conditions. FIG. 3.

Figure 4:
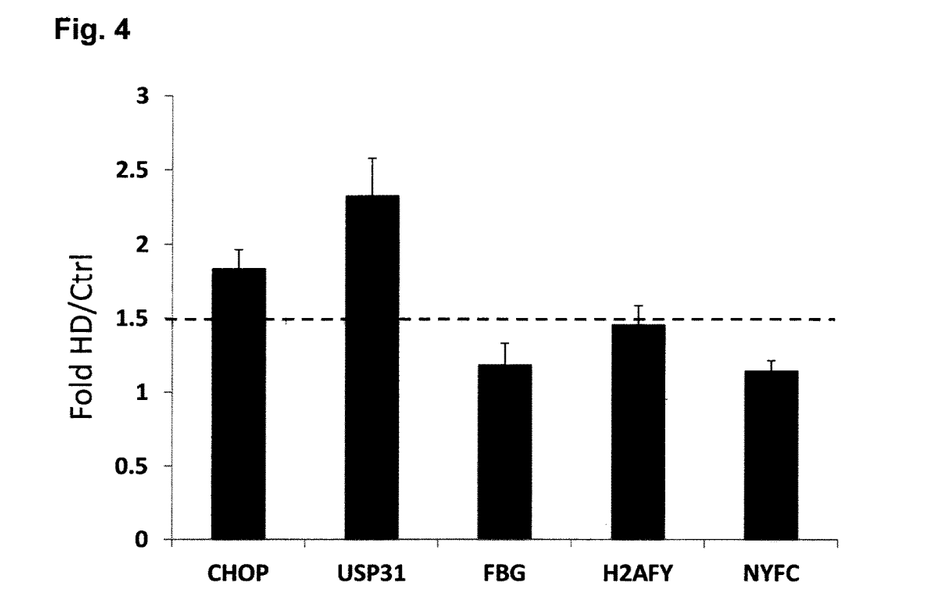
FIG. 4. Induction of the cloned, gene promoter sequences as demonstrated by the expression of a reporter gene (Luciferase).

Promoter constructs shown in Attachment 4 were transiently transfected into control or Huntington's disease-derived cultured fibroblast cells. We observed increased activity of the cloned gene promoter sequences in Huntington's disease fibroblasts when compared to control fibroblast cells. FIG. 4.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An expression cassette comprising
a promoter sequence consisting of a nucleic acid of between 500 and 1700 nucleotides in length, that is at least 90% identical to a polynucleotide sequence of at least 500 nucleotides of SEQ ID NO: 1, SEQ ID NO:2, SEQ ID NO:3, or SEQ ID NO:7; or
a promoter sequence consisting of a nucleic acid of between 600 and 1700 nucleotides in length, that is at least 90% identical to a polynucleotide sequence of at least 600 nucleotides of SEQ ID NO:4; and
wherein the promoter is operably linked to a preselected DNA segment encoding a protein or heterologous RNA transcript.

2. The expression cassette of claim 1, wherein the nucleic acid is at least 95% identical to a polynucleotide sequence of at least 500 nucleotides of SEQ ID NO: 1, SEQ ID NO:2, SEQ ID NO:3, or SEQ ID NO:7, or is at least 95% identical to a polynucleotide sequence of at least 600 nucleotides of SEQ ID NO:4.

3. The expression cassette of claim 1, wherein the preselected DNA segment encodes a therapeutic composition.

4. The expression cassette of claim 3, wherein therapeutic composition is an RNAi molecule.

5. A vector comprising the expression cassette of claim 1.

6. The vector of claim 5, wherein the vector is an adeno-associated virus (AAV) vector.

7. An isolated transformed cell comprising the expression cassette of claim 1.

8. The isolated transformed cell of claim 7, wherein the host cell is a eukaryotic cell.

9. A method for producing transformed cells comprising the steps of (i) introducing into cells the expression cassette of claim 1 so as to yield transformed cells, and (ii) identifying or selecting a transformed cell line.

10. The method of claim 9, wherein the DNA segment is expressed so as to impart a phenotypic characteristic to the transformed cells.

11. The method of claim 9, wherein the transformed cells exhibit significantly increased expression of the DNA segment when introduced into the cells derived from Huntington's disease patients as compared to cells derived from control individuals.

12. An isolated transformed cell made by the method of claim 9.

13. A method of treating a neurodegenerative disease in a mammal comprising administering the vector of claim 5, wherein the DNA segment encodes a therapeutic protein or heterologous RNA transcript.

14. The expression cassette of claim 1, wherein the polynucleotide is at least 90% identical to a polynucleotide sequence of at least 500 nucleotides of SEQ ID NO: 1.

15. The expression cassette of claim 1, wherein the polynucleotide is at least 90% identical to a polynucleotide sequence of at least 500 nucleotides of SEQ ID NO: 2.

16. The expression cassette of claim 1, wherein the polynucleotide is at least 90% identical to a polynucleotide sequence of at least 500 nucleotides of SEQ ID NO: 4.

17. The expression cassette of claim 1, wherein the polynucleotide is at least 90% identical to a polynucleotide sequence of at least 600 nucleotides of SEQ ID NO: 4.

18. The expression cassette of claim 1, wherein the polynucleotide is at least 90% identical to a polynucleotide sequence of at least 500 nucleotides of SEQ ID NO: 7.

* * * * *

UNITED STATES PATENT AND TRADEMARK OFFICE
CERTIFICATE OF CORRECTION

PATENT NO. : 10,105,450 B2
APPLICATION NO. : 14/776421
DATED : October 23, 2018
INVENTOR(S) : Beverly L. Davidson, Edgardo Rodriguez and Alejandro Mas Monteys It is certified that error appears in the above-identified patent and that said Letters Patent is hereby corrected as shown below:

In the Claims

Column 24, Line 14, Claim 16, please delete "of SEQ ID NO: 4." and insert -- of SEQ ID NO: 3. -- therefor.

Signed and Sealed this
First Day of October, 2019

Andrei Iancu
*Director of the United States Patent and Trademark Office*